United States Patent
Jia et al.

(10) Patent No.: US 11,547,130 B2
(45) Date of Patent: Jan. 10, 2023

(54) NANOCOMPOSITE BACTERIOSTATIC MATERIAL AND A PREPARATION METHOD AND AN APPLICATION THEREOF

(71) Applicant: Tianjin University of Science and Technology, Tianjin (CN)

(72) Inventors: Shiru Jia, Tianjin (CN); Jiandong Cui, Tianjin (CN); Zhilei Tan, Tianjin (CN); Cheng Zhong, Tianjin (CN); Yang Liu, Tianjin (CN); Qiaozhen Luo, Tianjin (CN); Xiaona Li, Tianjin (CN); Yuxiao Feng, Tianjin (CN); Baoting Sun, Tianjin (CN); Le Zhong, Tianjin (CN)

(73) Assignee: Tianjin University of Science and Technology, Tianjin (CN)

( * ) Notice: Subject to any disclaimer, the term of this patent is extended or adjusted under 35 U.S.C. 154(b) by 378 days.

(21) Appl. No.: 16/816,252

(22) Filed: Mar. 12, 2020

(65) Prior Publication Data
US 2020/0207876 A1   Jul. 2, 2020

(30) Foreign Application Priority Data
Sep. 20, 2019   (CN) .......................... 201910891851.2

(51) Int. Cl.
| | | |
|---|---|---|
| C07K 17/02 | (2006.01) | |
| B82Y 30/00 | (2011.01) | |
| A23L 3/3463 | (2006.01) | |
| A23B 4/20 | (2006.01) | |
| A23B 7/154 | (2006.01) | |
| B82Y 5/00 | (2011.01) | |
| B82Y 40/00 | (2011.01) | |

(52) U.S. Cl.
CPC ............ *A23L 3/34635* (2013.01); *A23B 4/20* (2013.01); *A23B 7/154* (2013.01); *C07K 17/02* (2013.01); *B82Y 5/00* (2013.01); *B82Y 30/00* (2013.01); *B82Y 40/00* (2013.01)

(58) Field of Classification Search
CPC ...... A23L 3/34635; B82Y 30/00; C07K 17/02
See application file for complete search history.

(56) References Cited

FOREIGN PATENT DOCUMENTS

| CN | 107668474 A | * | 2/2018 | ........... A23L 3/3526 |
|---|---|---|---|---|
| CN | 108456241 | | 8/2018 | |

OTHER PUBLICATIONS

Chang, CN-107668474-A (Feb. 2018), English Abstract.*
Preparation of ZIF-8 and its application as carrier for bactericidal drug, Aug. 31, 2018, Gao Jinlong, et., al.

* cited by examiner

*Primary Examiner* — Randy Boyer

(57) ABSTRACT

The present invention discloses a novel nano-composite antibacterial material and a preparation method and an application thereof, and belongs to the technical field of preservative materials. The novel nano-composite antibacterial material disclosed by the present invention is prepared by mixing a dimethylimidazole solution, deionized water and a zinc nitrate solution to prepare a metal-organic framework carrier, compositing with nisin to form a nano antibacterial composite material, separating out from a solution in a precipitate form, centrifuging, removing a supernatant, cleaning and re-suspending with the deionized water. The novel nano-composite antibacterial material prepared by the present invention has an antibacterial effect superior to nisin having a same concentration. The present invention prominently improves an antibacterial activity and thermostability of the nisin under neutral and slightly alkaline conditions, effectively promotes antibacterial property and a usable range of the nisin, and further expands an application field of the metal-organic framework carrier.

9 Claims, 1 Drawing Sheet

(a) (b)

(a) (b)

NANOCOMPOSITE BACTERIOSTATIC MATERIAL AND A PREPARATION METHOD AND AN APPLICATION THEREOF

FIELD OF TECHNOLOGY

The present invention belongs to the technical field of antiseptic materials, and specifically relates to a novel nano-composite antibacterial material and a preparation method and an application thereof.

BACKGROUND

Nisin is also referred to as nizyna or is transliterated as Nixin. It is a polypeptide substance generated by *streptococcus lactis*, consists of 34 amino acid residues and has a molecular weight of about 3500 Da. The nisin may inhibit most gram positive bacteria, has a strong inhibition effect to a spore of *Bacillus*, and thus is widely applied to food industry as a food antiseptic agent. The nisin is hydrolyzed into amino acid quickly under the action of a physiological pH condition and an α-chymotrypsin of a human body after being eaten. It does not change a normal flora in an intestinal tract of the human body and occur a resistant problem like other antibiotics, and even not occur a crossing resistance with the other antibiotics. The nisin is a natural food preservative with high effectiveness, no toxicity, safety and no side effect. However, the natural nisin has different antibacterial activities under different temperatures and different pH values. The nisin has a good antibacterial effect under a room-temperature acidic condition but the antibacterial effect is greatly reduced under a high-temperature condition. And under an alkaline condition, the antibacterial activity of the nisin is also greatly reduced. Moreover, it is difficult for the natural nisin to keep a long-acting antibacterial activity. All of these defects limit the application of the nisin.

Chinese patent application CN 107668474 A discloses a nisin nanometer particle as well as a preparation method and an application thereof, which improves the activity of the nisin but has short-term antibacterial effect, and unstable antibacterial property under the alkaline condition. Chinese patent application CN 106962498A discloses a nisin/chitosan nano particle antibacterial film, a preparation method and an application. The preparation method is complex, the cost is high, and the technical requirement is high, all of which become non-negligible key points. Chinese patent application CN 107027810A discloses a nisin cyclodextrin inclusion complex and a preparation method thereof, which improves thermostability of the nisin but has an unconspicuous effect under the alkaline condition. Chinese patent CN 103355730 B discloses a nisin composite biological preservative and a preparation method thereof, which uses more additives to improve stability of the nisin but has a complex preparation process due to the more additives. Chinese patent application CN 109453391 A discloses a method for preparing an external application gel from gellan gum and nisin and an application thereof. However, the antibacterial activity is not improved obviously. Chinese patent application CN 109430674 A discloses a preparation method of N-succinyl-chitosan immobilized nisin and purple *perilla* oil films, which overcomes the defect that the nisin is unstable under a neutral condition. Chinese patent application CN 109452290 A discloses a combined germicide containing benziothiazolinone and nisin and an application, which may be used for preventing some diseases of fruit trees. However, these technologies have various problems of unstable antibacterial activity, complex preparation, high cost and so on.

SUMMARY

The present invention provides a nisin nano-composite antibacterial material with safety, reliability, good biological property and high thermostability and a preparation method thereof.

The technical solutions used by the present invention are as follows.

A method for preparing a novel nano-composite antibacterial material includes the following steps:

(1) preparing a nisin solution having a concentration of 1-30 g/L, a solvent being water;

(2) adding a 0.5-1.0 mol/L dimethylimidazole solution, deionized water and a 0.1-0.8 mol/L zinc nitrate solution in sequence according to a volume ratio of (5-20):1:1 for mixing, stirring for 30-60 min, centrifuging to take a precipitate, and cleaning to obtain a metal-organic framework carrier; and (3) adding the nisin solution to the metal-organic framework carrier, stirring for 1-2 h, centrifuging a reacted product, removing a supernatant, cleaning a precipitate, and adding the deionized water for vortex suspension to obtain the nano-composite antibacterial material suspension having a concentration of 10-15 g/L.

Preferably, the titer of the nisin in the step (1) is (0.9-1.3)*$10^6$ IU/g.

In the step (2), the concentration of the dimethylimidazole solution may be 0.5 mol/L, 0.6 mol/L, 0.7 mol/L, 0.8 mol/L, 0.9 mol/L and 1.0 mol/L.

Preferably, the concentration of the dimethylimidazole solution in the step (2) is 0.8-1.0 mol/L.

In the step (2), the concentration of the zinc nitrate solution may be 0.1 mol/L, 0.2 mol/L, 0.3 mol/L, 0.4 mol/L, 0.5 mol/L, 0.6 mol/L, 0.7 mol/L and 0.8 mol/L.

Preferably, the concentration of the zinc nitrate solution in the step (2) is 0.3-0.5 mol/L, and the metal-organic framework carrier formed under the condition of this range has a large volume, a plump shape and a large specific surface area, and may adsorb more nisin.

Preferably, the volume ratio of the dimethylimidazole solution to the deionized water to the zinc nitrate solution is (8-15):(1-3):(1-3) in the step (2), and under the condition of this proportion, the synthesis of the metal framework is better.

The volume ratio of the dimethylimidazole solution to the deionized water to the zinc nitrate solution may be 8:1:1, 9:1:1, 10:1:1, 11:1:1, 12:1:1, 13:1:1, 14:1:1, 15:1:1, 8:1:2, 9:1:2, 10:1:2, 11:1:2, 12:1:2, 13:1:2, 14:1:2, 15:1:2, 8:1:3, 9:1:3, 10:1:3, 11:1:3, 12:1:3, 13:1:3, 14:1:3, 15:1:3, 8:2:1, 9:2:1, 10:2:1, 11:2:1, 12:2:1, 13:2:1, 14:2:1, 15:2:1, 8:3:1, 9:3:1, 10:3:1, 11:3:1, 12:3:1, 13:3:1, 14:3:1, and 15:3:1.

More preferably, the volume ratio of the dimethylimidazole solution to the deionized water to the zinc nitrate solution is (11-15):(1-2):(1-2) in the step (2).

Preferably, in the step (2), a stirring rotational speed is 8000-12000 rpm, and time is 5-10 min; and under this centrifugal condition, the centrifugation is complete, and an unnecessary substance not participated in reaction is removed easily.

Preferably, in the step (2), a reaction condition during stirring is 20-30° C.

Preferably, in the step (3), a volume ratio of an added amount of the nisin solution to the dimethylimidazole solution in the step (2) is 1:(1-2). Within a range of this added proportion of the nisin, the metal framework has a good absorption effect to the nisin.

Preferably, a pH value of the nano-composite antibacterial material suspension in the step (3) is 7.0-9.0.

Another object of the present invention is to provide a novel nano-composite antibacterial material prepared with any one of the above-mentioned preparation methods.

Another object of the present invention is to provide an application of the above-mentioned novel nano-composite antibacterial material in antibacterial field.

A pH application range of the novel nano-composite antibacterial material in the antibacterial field is 6.5-9.0.

Compared with the prior art, the present invention has the following beneficial effects:

1. The present invention first proposes a method for preparing a novel nano-composite antibacterial material. A complex is got after the reaction between the prepared metal-organic framework carrier and the nisin in which the nisin is absorbed by the metal-organic framework carrier. The formed nano-composite material is prepared by separating out from a solution in a precipitate form, centrifuging, removing a supernatant, cleaning and re-suspending with deionized water. The novel nano-composite antibacterial material has an antibacterial effect superior to the free nisin having a same concentration. The metal-organic framework carrier is often usually used to adsorb an embedding enzyme, a gas and other substances. The present invention first combines the metal-organic framework carrier with the nisin; and by the combination between the metal-organic framework carrier and the nisin, the present invention not only provides an novel nano-composite antibacterial material, but also effectively improves stability of the nisin under neutral and slightly alkaline conditions, prominently promotes antibacterial property and a usable range of the nisin, and further expands an application field of the metal-organic framework carrier.

The metal-organic framework is a crystalline porous material having a periodic network structure and formed by self-assembly and mutual connection of an inorganic metal center (a metal ion or a metal cluster) and a bridged organic ligand. It is also an organic-inorganic hybrid material and also referred to as a coordination polymer. Different from an inorganic porous material and a common organic complex, the metal-organic framework has the characteristics of rigidity of an inorganic material and flexibility of an organic material. With a large porosity, a large specific surface area and a diverse structure, the nisin is adsorbed to a surface of the metal-organic framework or embedded into a pore of the metal-organic framework, to achieve the effects of protecting the nisin and improving the activity of the nisin. In addition, a pH value of the prepared nano-composite antibacterial material is 7.0-9.0, which breaks the limit that the nisin can only be used within an acidic condition.

The metal-organic framework carrier prepared by mixing a dimethylimidazole solution, deionized water and a zinc nitrate solution has slow release, can keep loading a target product for a long time, and can keep a function for a long term.

2. After being loaded with the nisin, the metal-organic framework carrier can protect the nisin well and may further expand the usable range of the nisin. Meanwhile, the antibacterial activity of the nisin may be released slowly, so that the nisin keeps the antibacterial activity for a long time. Particularly, by compositing the nisin, the metal-organic framework carrier prepared by the present invention may enable the nisin to have good antibacterial stability and thermostability in neutral and slightly alkaline environments, and thus effectively improves stability, antibacterial persistence and an antibacterial range of the nisin. Additionally, the present invention has a simple preparation method, high operability, and good antibacterial activity and stability.

However, the metal-organic framework carrier cannot be loaded with all biological antibacterial peptides substances. When the metal-organic framework carrier of the present invention is loaded with ε-polylysine, the antibacterial activity under the neutral and slightly alkaline conditions is not improved. That is, by adding a 0.5-1.0 mol/L dimethylimidazole solution, a ε-polylysine solution having a concentration of 10-30 mg/L and a 0.1-0.8 mol/L zinc nitrate solution in sequence according to a volume ratio of (5-20):1:1 for mixing, stirring for 30-60 min, centrifuging to take a precipitate, and cleaning to obtain an antibacterial composite material, re-suspending with water to obtain a nano-composite antibacterial material suspension having a concentration of 10-15 g/L, regulating a pH value with acetic acid respectively to 6.5, 7.0, 7.5 and 8.0. And taking 100 μL to carry out an antibacterial circle experiment same as a method in Embodiment example 4, a result shows that an antibacterial circle of the composite antibacterial material loaded with the ε-polylysine is the same as an antibacterial circle of an empty carrier or even smaller than the antibacterial circle of the empty carrier.

To sum up, the metal-organic framework carrier prepared by the present invention is not effective to all antibacterial peptides. The inventors of the present invention found by accident that the antibacterial material has notable antibacterial property to the nisin. Meanwhile, in a process when the nano-composite antibacterial material is prepared, the present invention improves the antibacterial property and the thermostability of the nisin in the neutral and slightly alkaline environments more effectively by designing a special proportion of the dimethylimidazole solution, the deionized water, the zinc nitrate solution and the nisin, and controlling a special condition in the preparation process.

DESCRIPTION OF THE EMBODIMENTS

Figure 1:
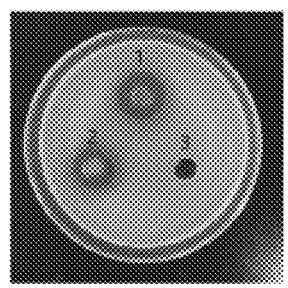
FIG. 1 is a measurement diagram of thermostability of a nano-composite antibacterial material according to Experimental example 4, where the (a) shows antibacterial circles corresponding to experimental group 1 and control groups 1, 3, wherein 1-embodimental group 1 (composite material), 2-control group 1 (empty carrier), and 3-control group 3 (free nisin, having a concentration of 10 g/L); and the (b) shows antibacterial circles corresponding to experimental group 2, and control groups 2, 4, wherein 1-experimental group 2 (composite material), 2-control group 2 (empty carrier), and 3-control group 4 (free nisin, having a concentration of 30 g/L).
Figure 1:
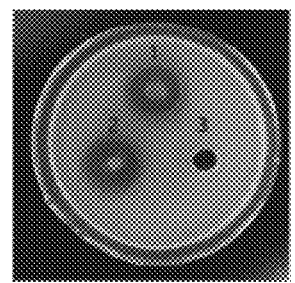

The present invention is described below through specific embodiments. Unless otherwise specified, the technical means used in the present invention are all methods known to those skilled in the art. In addition, the embodiments should be understood as being illustrative, rather than limiting the scope of the present invention. The essence and scope of the present invention are only defined by the claims. For those skilled in the art, without departing from the essence and scope of the present invention, various changes or modifications to the material composition and amount used in these embodiments also belong to the protection scope of the present invention. The present invention is further described below in combination with specific embodiments.

Embodiment 1 Preparation of Nisin Nano-Composite Antibacterial Material

The nisin nano-composite antibacterial material obtained by adsorption of nisin by the metal-organic framework carrier is prepared by the following steps:

(1) 10 mg of nisin having a molecular weight of about 3500 Da was dissolved in 10 mL of deionized water to prepare a nisin solution having a concentration of 1 g/L, the titer of the nisin being $0.9*10^6$ IU/g.

(2) 11 mL of 1.0 mol/L dimethylimidazole solution was added to a conical flask and placed onto a magnetic stirrer, then 2 mL of deionized water was added, 2 mL of 0.4 mol/L zinc nitrate solution was added, the mixed solution reacted at 20-30° C., was stirred for 30 min and was centrifuged at 8000 rpm for 10 min, a supernatant was removed, and the deionized water was used for cleaning to obtain a metal-organic framework carrier.

(3) The metal-organic framework carrier was placed into a conical flask and stirred uniformly on the magnetic stirrer; and then, 11 mL of nisin solution having the concentration of 1 g/L was added, and stirred for adsorption reaction with reference to an experimental method in which the carrier absorbs an enzyme. A reacted sample was centrifuged, a supernatant was removed, and after a precipitate was cleaned with the deionized water, the deionized water was added continuously for vortex suspension to prepare a milk white suspension having a concentration of 10 g/L, and obtain a nisin nano-composite antibacterial material suspension, a pH of the suspension being measured as 8.5.

Embodiment 2 Preparation of Nisin Nano-Composite Antibacterial Material

The nisin nano-composite antibacterial material obtained by adsorption of nisin by the metal-organic framework carrier is prepared by the following steps:

(1) 100 mg of nisin having a molecular weight of about 3500 Da was dissolved in 10 mL of deionized water to prepare a nisin solution having a concentration of 10 g/L, the titer of the nisin being $1.1*10^6$ IU/g.

(2) 12 mL of 0.8 mol/L dimethylimidazole solution was added to a conical flask and placed onto a magnetic stirrer, then 2 mL of deionized water was added, 1 mL of 0.3 mol/L zinc nitrate solution was added, the mixed solution reacted at 20-30° C., was stirred for 45 min and was centrifuged at a stirring rotational speed of 12000 rpm for 6 min, a supernatant was removed, and the deionized water was used for cleaning to obtain a metal-organic framework carrier.

(3) The metal-organic framework carrier was placed into the conical flask and stirred uniformly on the magnetic stirrer; and then, 10 mL of nisin solution having the concentration of 10 g/L was added, and stirred for adsorption reaction with reference to an experimental method in which the carrier absorbs an enzyme. A reacted sample was centrifuged, a supernatant was removed, and after a precipitate was cleaned with the deionized water, the deionized water was added continuously for vortex suspension to prepare a milk white suspension having a concentration of 15 g/L, and obtain a nisin nano-composite antibacterial material suspension, a pH of the suspension being measured as 8.16.

Embodiment 3 Preparation of Nisin Nano-Composite Antibacterial Material

The nisin nano-composite antibacterial material obtained by adsorption of nisin by the metal-organic framework carrier is prepared by the following steps:

(1) 300 mg of nisin having a molecular weight of about 3500 Da was dissolved in 10 mL of deionized water to prepare a nisin solution having a concentration of 30 g/L, the titer of the nisin being $1.0*10^6$ IU/g.

(2) 12 mL of 1.0 mol/L dimethylimidazole solution was added to a conical flask, the conical flask was placed onto a magnetic stirrer, 1 mL of deionized water was added, then 1 mL of 0.4 mol/L zinc nitrate solution was added, the mixed solution reacted at 20-30° C., was stirred for 60 min and was centrifuged at a stirring rotational speed of 9000 rpm for 8 min, a supernatant was removed, and the deionized water was used for cleaning to obtain a metal-organic framework carrier.

(3) The metal-organic framework carrier was placed into the conical flask and stirred uniformly on the magnetic stirrer; and then, 12 mL of nisin solution having the concentration of 30 g/L was added, and stirred for adsorption reaction with reference to an experimental method in which the carrier absorbs an enzyme. A reacted sample was centrifuged, a supernatant was removed, and after a precipitate was cleaned with the deionized water, the deionized water was added continuously for vortex suspension to prepare a milk white suspension having a concentration of 15 g/L, and obtain a nisin nano-composite antibacterial material suspension, a pH of the suspension being measured as 7.66.

Embodiment 4 Preparation of Nisin Nano-Composite Antibacterial Material

The nisin nano-composite antibacterial material obtained by adsorption of nisin by the metal-organic framework carrier is prepared by the following steps:

(1) A nisin solution having a concentration of 30 g/L was prepared, the titer of the nisin being $1.0*10^6$ IU/g.

(2) 0.8 mol/L dimethylimidazole solution, deionized water and 0.4 mol/L zinc nitrate solution were added to a conical flask in sequence according to a volume ratio of (11-12):(1-2):(1-2), the conical flask was placed onto a magnetic stirrer for mixing, the mixed solution reacted at 20-30° C., was stirred for 60 min, and was centrifuged at a stirring rotational speed of 8000-9000 rpm for 5-10 min, a supernatant was removed, and the deionized water was used for cleaning to obtain a metal-organic framework carrier.

(3) The metal-organic framework carrier was placed into the conical flask and uniformly stirred on the magnetic stirrer, and then the nisin solution having the concentration of 30 g/L was added, a volume ratio of an added amount of the nisin solution to the dimethylimidazole solution in the step (2) being 1:(1-2). The mixed solution was stirred for adsorption reaction with reference to an experimental method in which the carrier adsorbs an enzyme. A reacted sample was centrifuged, a supernatant was removed, and after a precipitate was cleaned with the deionized water, the deionized water was added continuously for vortex suspension to prepare a milk white suspension having a concentration of 14-15 g/L, and obtain a nisin nano-composite antibacterial material suspension.

and a bacteria solution was added, an initial pH value of the culture medium after the addition being 6.80.

Experimental group: 1 mL of nano-composite antibacterial material suspension prepared in Embodiment 1 of the present invention was added to an LB liquid culture medium, and a bacteria solution was added, an initial pH value of the culture medium after the addition being 7.16.

TABLE 1

Comparison of antibacterial property of nano-composite antibacterial material (the added concentration of nisin was 1 g/L)

| | Antibacterial agent | | | | | | | |
|---|---|---|---|---|---|---|---|---|
| | No-treatment Control group | | Control group 1 Metal-organic framework | | Control group 2 Nisin | | Experimental group Nano-composite material | |
| Culture time (h) | Colony count (CFU/mL) | pH value of bacteria solution | Colony count (CFU/mL) | pH value of bacteria solution | Colony count (CFU/mL) | pH value of bacteria solution | Colony count (CFU/mL) | pH value of bacteria solution |
| 4 | | | | | | | | |

Experimental Example 1 Comparison of Antibacterial Property of Nano-Composite Antibacterial Material (the Adsorbent Concentration of Nisin is 1 g/L)

In order to measure an antibacterial activity of the nisin nano-composite antibacterial material obtained by adsorption of nisin by the metal-organic framework carrier in Embodiment 1, a series of antibacterial tests are carried out:

*Bacillus subtilis* was selected as a strain for the antibacterial test. The *Bacillus subtilis* was cultured for overnight in a shake flask first, and a bacteria solution having a concentration of $10^8$ CFU/mL was selected as a seed solution for later use. Multiple 100 mL triangular flasks provided with 30 mL of LB liquid medium were taken, and sterilized for 20 min at 121° C. The triangular flasks were divided into four groups, three triangular flasks in each group for parallel test. 1 mL of suspension of the carrier adsorbed with nisin, 1 mL of empty carrier suspension, 1 mL of nisin solution and 1 mL of sterilized ultrapure water were added respectively to each group.

The *Bacillus subtilis* solution having the concentration of $10^8$ CFU/mL was inoculated to the above four groups as per an inoculum size of 2% (v/v), and respectively cultured for 4 h, 8 h, 12 h, 24 h and 28 h on a shaker, where a culture condition was 37° C. and 180 r/min. Then, a sample at every timing was taken, and a viable count in each shake flask was measured via a dilution spread plate method to embody the antibacterial activity.

The experiment was divided into four groups.

No-treatment Control group: 1 mL of sterilized ultrapure water and bacteria solution were added to an LB liquid culture medium, an initial pH value of the culture medium after the addition being 6.85.

Control group 1: 1 mL of metal-organic framework carrier obtained in step (2) of Embodiment 1 was added to an LB liquid culture medium, and a bacteria solution was added, an initial pH value of the culture medium after the addition being 7.08.

Control group 2: 1 mL of nisin solution having a concentration of 1 g/L was added to an LB liquid culture medium, Measured results show that when the concentration of viable bacteria in the shake flask is higher, the antibacterial effect is poorer. When the concentration of viable bacteria in the shake flask is lower, it is indicated that the antibacterial effect of the antibacterial agent is better. As can be seen from data, the concentration of viable bacteria in the shake flask added with the nisin at 4 h in culture reaches to $10^4$ CFU/mL or more, that in the shake flask added with the nano-composite material is $10^3$ CFU/mL, that in the shake flask added with the empty carrier is $10^5$ CFU/mL, and the No-treatment Control group is up to a level of $10^7$ CFU/mL. Therefore, it can be seen that the nano-composite material has a better antibacterial effect than other antibacterial agents. At 8-12 h in culture, a content of bacteria in the shake flask added with the nisin reaches to $10^7$ CFU/mL or more, which indicates that the nisin has lost bacteriostatic action at 8 h. However, the concentration of bacteria in the flasks added with the nano-composite material and the empty carrier are respectively keeps at $10^3$ CFU/mL and $10^5$ CFU/mL, which indicates that the nano-composite material still has a high antibacterial activity. At 24-28 h, the concentration of bacteria in the shake flask added with the empty carrier is up to $10^8$ CFU/mL or more, and similar to the colony count of the No-treatment Control group, which indicates that the empty carrier has basically lost an antibacterial characteristic at this time. However, the concentration of bacteria after the nano-composite material is added still keeps at $10^3$ CFU/mL, which indicates that the nano-composite material still has the high antibacterial activity at 28 h, excellent antibacterial property to the *Bacillus subtilis* and a slow-release effect to the nisin, and may keep a long-acting antibacterial function of the nisin.

Experimental Example 2 Comparison of Antibacterial Property of Nano-Composite Antibacterial Material (the Adsorbent Concentration of Nisin is 10 g/L)

In order to measure an antibacterial activity of the metal-organic framework carrier adsorbing nisin nano-composite antibacterial material in Embodiment 2, a series of antibacterial tests are carried out:

Bacillus subtilis was selected as a strain for the antibacterial test. The Bacillus subtilis was cultured for overnight in a shake flask first, and a bacteria solution having a concentration of $10^8$ CFU/mL was selected as a seed solution for later use. Multiple 100 mL triangular flasks provided with 30 mL of LB liquid medium were taken, and sterilized for 20 min at 121° C. The triangular flasks were divided into four groups, three triangular flasks in each group for parallel test. 1 mL of suspension of the carrier adsorbed with nisin, 1 mL of empty carrier suspension, 1 mL of nisin solution and 1 mL of sterilized ultrapure water were added respectively to each group.

The Bacillus subtilis solution having the concentration of $10^8$ CFU/mL was inoculated to the above four groups as per an inoculum size of 2% (v/v), and respectively cultured for 4 h, 8 h, 12 h, 24 h and 28 h on a shaker, where a culture condition was 37° C. and 180 r/min, for sampling. Then, a sample was taken, and a viable count in each shake flask at every moment was measured via a dilution spread plate method to embody the antibacterial activity.

The experiment was divided into four groups.

No-treatment Control group: same as the No-treatment Control group in the experimental example 1

Control group 1: 1 mL of metal-organic framework carrier obtained in the step (2) of Embodiment 2 was added to an LB liquid culture medium, and a bacteria solution was added, an initial pH value of the culture medium after the addition being 7.04.

Control group 2: 1 mL of nisin solution having a concentration of 10 g/L was added to an LB liquid culture medium, and a bacteria solution was added, an initial pH value of the culture medium after the addition being 6.82.

Experimental group: 1 mL of nano-composite antibacterial material suspension prepared in Embodiment 2 of the present invention was added to an LB liquid culture medium, and a bacteria solution was added, an initial pH value of the culture medium after the addition being 7.14.

The experimental data are as follows:

antibacterial activity of the nisin having a same concentration has been greatly reduced, and the antibacterial effect of the empty carrier has basically lost. However, the antibacterial activity of the nano-composite antibacterial material is still notable.

Experimental Example 3 Comparison of Antibacterial Property of Nano-Composite Antibacterial Material (the Adsorbent Concentration of Nisin is 30 g/L)

In order to measure an antibacterial activity of the metal-organic framework carrier adsorbing nisin nano-composite antibacterial material in Embodiment 3, a series of antibacterial tests are carried out:

Bacillus subtilis was selected as a strain for the antibacterial test. The Bacillus subtilis was cultured for overnight in a shake flask first, and a bacteria solution having a concentration of $10^8$ CFU/mL was selected as a seed solution for later use. Multiple 100 mL triangular flasks provided with 30 mL of LB liquid medium were taken, and sterilized for 20 min at 121° C. The triangular flasks were divided into four groups, three triangular flasks in each group for parallel test. 1 mL of suspension of the carrier adsorbed with nisin, 1 mL of empty carrier suspension, 1 mL of nisin solution and 1 mL of sterilized ultrapure water were added respectively to each group.

The Bacillus subtilis solution having the concentration of $10^8$ CFU/mL was inoculated to the above four groups as per an inoculum size of 2% (v/v), and respectively cultured for 4 h, 8 h, 12 h, 24 h and 28 h on a shaker, where a culture condition was 37° C. and 180 r/min, for sampling. Then, a sample was taken, and a viable count in each shake flask at every moment was measured via a dilution spread plate method to embody the antibacterial activity.

The experiment was divided into four groups.

No-treatment Control group: same as the No-treatment Control group in the experimental example 1

Control group 1: 1 mL of metal-organic framework carrier obtained in the step (2) of Embodiment 3 was added to an LB liquid culture medium, and a bacteria solution was added, an initial pH value of the culture medium after the addition being 7.01.

Control group 2: 1 mL of nisin solution having a concentration of 30 g/L was added to an LB liquid culture medium, and a bacteria solution was added, an initial pH value of the culture medium after the addition being 6.79.

Experimental group: 1 mL of nano-composite antibacterial material suspension prepared in Embodiment 3 of the

TABLE 2

Comparison of antibacterial property of nano-composite antibacterial material (the added concentration of nisin was 10 g/L)

| Culture time (h) | Antibacterial agent | | | | | | | |
|---|---|---|---|---|---|---|---|---|
| | No-treatment Control group | | Control group 1 Metal-organic framework | | Control group 2 Nisin | | Experimental group Nano-composite material | |
| | Colony count (CFU/mL) | pH value of bacteria solution | Colony count (CFU/mL) | pH value of bacteria solution | Colony count (CFU/mL) | pH value of bacteria solution | Colony count (CFU/mL) | pH value of bacteria solution |

Experimental results show that when the concentration of the nisin is improved to 10 g/L, the antibacterial effect of the nano-composite material is further improved. At 16 h, the present invention was added to an LB liquid culture medium, and a bacteria solution was added, an initial pH value of the culture medium after the addition being 7.15.

The experimental data are as follows:

TABLE 3

Comparison of antibacterial property of nano-composite antibacterial material (the added concentration of nisin was 30 g/L)

| Culture time (h) | No-treatment Control group | | Antibacterial agent Control group 1 Metal-organic framework | | Control group 2 Nisin | | Experimental group Nano-composite material | |
|---|---|---|---|---|---|---|---|---|
| | Colony count (CFU/mL) | pH value of bacteria solution | Colony count (CFU/mL) | pH value of bacteria solution | Colony count (CFU/mL) | pH value of bacteria solution | Colony count (CFU/mL) | pH value of bacteria solution |

Experimental results show that when the absorbent concentration of the nisin is improved to 30 g/L, the viable count in previous 12 h is further reduced, and the antibacterial activity of the nisin nano-composite antibacterial material prepared in the present invention is further improved.

It is to be noted that the nisin nano-composite antibacterial material prepared in Embodiment 4 of the present invention has a similar technical effect with Embodiment 3 in antibacterial property.

Experimental Example 4 Measurement of Thermostability of Nano-Composite Material In order to measure the thermostability of the nano-composite material prepared in the present invention under a neutral condition, the material is subjected to heat treatment under the neutral condition, to measure antibacterial property.

The following groups were provided: experimental group 1: nano-composite material prepared via steps (1), (2) and (3) of Embodiment 2.

Experimental group 2: nano-composite material prepared via steps (1), (3) and (3) of Embodiment 3.

Control group 1: empty carrier prepared via step (2) of Embodiment 2.

Control group 2: empty carrier prepared via step (2) of Embodiment 3.

Control group 3: nisin prepared via step (1) of Embodiment 2 (having a concentration of 10 g/L)

Control group 4: nisin prepared via step (1) of Embodiment 3 (having a concentration of 30 g/L)

The pH value of each material in the above groups was regulated to 7 with HCl and subjected to the heat treatment at 60° C. for 30 min; and with the use of an antibacterial circle experimental method, the antibacterial effect was determined according to a diameter of an antibacterial circle.

*Bacillus subtilis* was cultured for overnight in a shake flask, and a bacteria solution having a concentration of $10^8$ CFU/mL was selected as a seed solution for later use. The seed solution was inoculated as per 2% of inoculum size to an LB semi-solid culture medium sterilized at about 50° C. under a sterile condition, and mixed quickly and uniformly to pour into a culture dish, 20 mL being poured into each culture dish. Upon solidification, three holes were punched on the culture dish by a puncher, and different antibacterial samples were respectively added to each hole, an added amount of each group being 150 μL. Upon the completion, each culture dish was placed into a constant temperature incubator at 37° C., and cultured for 16 h to observe and measure a size of the antibacterial circle. FIG. 1 shows the picture of an experiment result of an antibacterial circle method.

TABLE 4

Diameter of antibacterial circle for measurement of thermostability of nano-composite antibacterial material (Unit: mm)

| Group | Antibacterial circle (mm) | Group | Antibacterial circle (mm) | Group | Antibacterial circle (mm) |
|---|---|---|---|---|---|
| Experimental group 1 | | Control group 1 | | Control group 3 | |
| Experimental group 2 | | Control group 2 | | Control group 4 | |

It can be seen from the antibacterial experiment that the composite material prepared in the present invention has notable thermostability. Compared with free nisin that is easily inactivated with high-temperature treatment under the neutral condition, by treating the nisin with the method of the present invention to prepare the nano-composite material or a composite biological preservative, the stability under neutral and alkaline conditions may be improved (experimental groups 1, 2). Although the empty carrier in the control groups 1, 2 also has the antibacterial property, it can also be seen that the experimental groups 1, 2 are obviously higher than the control groups 1, 2 in antibacterial property.

It is to be noted that the nisin nano-composite antibacterial material prepared in Embodiment 4 of the present invention has a similar technical effect with Embodiment 3 (experimental group 2) in antibacterial property.

Experimental Example 5 Influence of Zinc Nitrate on Carrier Form

Figure 2:
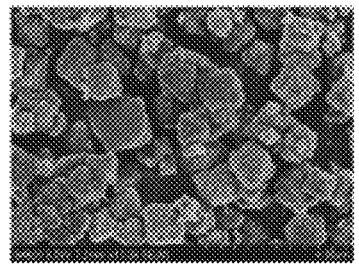
FIG. 2 shows a micromorphological structure of a metal-organic framework carrier under a scanning electron microscope, where the (a) is the metal-organic framework carrier prepared from a zinc nitrate solution having a concentration of 0.4 mol/L, and the (b) is the metal-organic framework carrier prepared from a zinc nitrate solution having a concentration of 0.7 mol/L, the amplification factor being 13,000 times.
Figure 2:
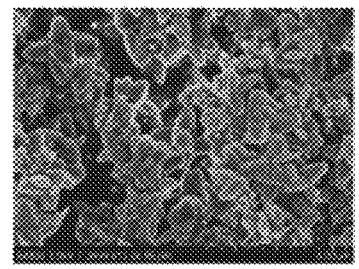

The form of the metal-organic framework carrier has an important influence on an adsorbing capacity of the nisin, and the concentration of the zinc nitrate has a certain influence on a carrier form. Hence, the following groups were provided:

Experimental group 1: 0.4 mol/L zinc nitrate solution.
Experimental group 2: 0.7 mol/L zinc nitrate solution.
The specific preparation method is as follows:

10 mL of 1.0 mol/L dimethylimidazole solution was respectively added to conical flasks, the conical flasks were placed onto a magnetic stirrer, then 1 mL of deionized water was added, 1 mL of 0.4 mol/L zinc nitrate solution and 1 mL of 0.7 mol/L zinc nitrate solution were added respectively. The mixed solution reacted at 20-30° C., was stirred for 30 min and was centrifuged. A supernatant was removed, and the deionized water was used for cleaning to obtain two metal-organic framework carriers. Referring to FIG. 2, the picture a is a photo of the metal-organic framework carrier, prepared with the 0.4 mol/L zinc nitrate solution, under a scanning electron microscope, and the picture b is a photo of the metal-organic framework carrier, prepared with the 0.7 mol/L zinc nitrate solution, under the scanning electron microscope. The amplification factor is 13000 times.

As can be seen from the figure, particle sizes of the two carriers are basically the same and are about 1 μm. For the experimental group 1, the metal-organic framework carrier prepared with the zinc nitrate solution having the concentration of 0.4 mol/L is of a square shape, has a plump form and a large specific surface area, may adsorb more nisin under the condition of a same concentration, and has an adsorbing capacity superior to the experimental group 2. For the experimental group 2, the metal-organic framework carrier prepared with the zinc nitrate solution having the concentration of 0.7 mol/L is of a cruciate flower shape and a slightly small specific surface area but may also adsorb the nisin.

The above are only preferred embodiments of the present invention. It should be pointed out that the person of ordinary skill in the art may further make multiple improvements and modifications without departing from the principle of the present invention, and those improvements and modifications are also should be considered as the protection scope of the present invention.

What is claimed is:

1. A method for preparing a nano-composite antibacterial material, comprising the following steps:
    (1) preparing a nisin solution having a concentration of 1-30 g/L, a solvent being water;
    (2) adding a 0.5-1.0 mol/L dimethylimidazole solution, deionized water and a 0.1-0.8 mol/L zinc nitrate solution in sequence according to a volume ratio of (5-20):1:1 for mixing, stirring for 30-60 min, centrifuging to take a precipitate, and cleaning to obtain a metal-organic framework carrier; and
    (3) adding the nisin solution to the metal-organic framework carrier, stirring for 1-2 h, centrifuging a reacted sample, removing a supernatant, cleaning a precipitate, and adding deionized water to be subjected to vortex suspension to obtain a nano-composite antibacterial material suspension having a concentration of 10-15 g/L.

2. The method for preparing the nano-composite antibacterial material according to claim 1, wherein the titer of the nisin in the step (1) is $(0.9-1.3)*10^6$ IU/g.

3. The method for preparing the nano-composite antibacterial material according to claim 1, wherein the concentration of the dimethylimidazole solution in the step (2) is 0.8-1.0 mol/L.

4. The method for preparing the nano-composite antibacterial material according to claim 1, wherein the concentration of the zinc nitrate solution in the step (2) is 0.3-0.5 mol/L.

5. The method for preparing the nano-composite antibacterial material according to claim 1, wherein the volume ratio of the dimethylimidazole solution to the deionized water to the zinc nitrate solution in the step (2) is (8-15):(1-3):(1-3).

6. The method for preparing the nano-composite antibacterial material according to claim 5, wherein the volume ratio of the dimethylimidazole solution to the deionized water to the zinc nitrate solution in the step (2) is (11-15):(1-2):(1-2).

7. The method for preparing the nano-composite antibacterial material according to claim 1, wherein in the step (2), a stirring rotational speed is 8000-12000 rpm, and stirring time is 5-10 min.

8. The method for preparing the nano-composite antibacterial material according to claim 1, wherein in the step (3), a volume ratio of an added amount of the nisin solution to the dimethylimidazole solution in the step (2) is 1:(1-2).

9. A nano-composite antibacterial material prepared with the preparation method according to claim 1.

* * * * *